US010111974B1

(12) United States Patent
Dennis et al.

(10) Patent No.: US 10,111,974 B1
(45) Date of Patent: Oct. 30, 2018

(54) METHOD AND APPARATUS FOR ON-SITE MICROBIAL REMEDIATION AND SANITIZATION OF HOUSEHOLD ITEMS

(71) Applicants: Donald Patrick Dennis, Atlanta, GA (US); William David Meadows, Marietta, GA (US)

(72) Inventors: Donald Patrick Dennis, Atlanta, GA (US); William David Meadows, Marietta, GA (US)

(73) Assignee: Vacu Fog LLC, Atlanta, GA (US)

( * ) Notice: Subject to any disclaimer, the term of this patent is extended or adjusted under 35 U.S.C. 154(b) by 0 days.

(21) Appl. No.: 15/593,920

(22) Filed: May 12, 2017

(51) Int. Cl.
  *B65B 5/04* (2006.01)
  *A61L 2/22* (2006.01)
  *B65B 7/02* (2006.01)
  *B65B 31/00* (2006.01)

(52) U.S. Cl.
  CPC ............ *A61L 2/22* (2013.01); *B65B 5/045* (2013.01); *B65B 7/02* (2013.01); *B65B 31/00* (2013.01); *A61L 2202/15* (2013.01); *A61L 2202/23* (2013.01)

(58) Field of Classification Search
  CPC ........... B65B 5/045; B65B 7/02; B65B 31/00; A61L 2/22; A61L 2202/15; A61L 2202/23
  USPC ........................................................ 53/425
  See application file for complete search history.

(56) References Cited

U.S. PATENT DOCUMENTS

| | | | | | |
|---|---|---|---|---|---|
| 4,312,171 | A | * | 1/1982 | Vadas | B65B 31/041 53/403 |
| 5,851,485 | A | * | 12/1998 | Lin | A61L 2/14 422/27 |
| 7,273,594 | B2 | * | 9/2007 | Lin | A61L 2/14 422/292 |
| 7,415,811 | B2 | * | 8/2008 | Gottlieb | A61L 2/08 53/425 |
| 7,631,760 | B2 | * | 12/2009 | Guelzow | A61F 2/0095 206/204 |
| 7,803,316 | B2 | * | 9/2010 | Lin | A61L 2/208 134/22.12 |
| 8,323,562 | B2 | * | 12/2012 | Schorr | B65D 81/2023 250/453.11 |
| 9,050,385 | B2 | * | 6/2015 | Weinberger | A61L 2/20 |

(Continued)

*Primary Examiner* — Sameh Tawfik
(74) *Attorney, Agent, or Firm* — Sanford Jay Asman

(57) ABSTRACT

A system and method for on-site remediation and sanitization of household items preferably uses a HEPA vacuum to remove surface microbials from the item being remediated. The item is then placed into a sealable plastic vacuum bag having a connection port that allows a vacuum to remove air from the bag, collapsing the bag over the item (which has first been braced to the extent necessary to prevent damage to the item). Once the air has been extracted from the vacuum bag air is introduced into the bag, preferably by using a blower, whereby a fogger can be used to introduce a remediating fog into the bag with the remediating fog surrounding the item. Next, the vacuum is used to again collapse the bag around the item, thereby infusing the remediating fog into the item. In a preferred embodiment of the invention the steps of inflating, fogging, and collapsing may be repeated one or more times to thoroughly infuse the remediating solution into the item, after which the item is removed from the vacuum bag.

9 Claims, 2 Drawing Sheets

(56) References Cited

U.S. PATENT DOCUMENTS

| | | | | |
|---|---|---|---|---|
| 2004/0062692 | A1* | 4/2004 | Lin | A61L 2/07 |
| | | | | 422/297 |
| 2007/0192986 | A1* | 8/2007 | Garcia | A47L 9/00 |
| | | | | 15/339 |
| 2007/0283986 | A1* | 12/2007 | Baum | A01M 13/003 |
| | | | | 134/201 |
| 2011/0094681 | A1* | 4/2011 | Bisges | A61L 2/14 |
| | | | | 156/345.26 |
| 2012/0304381 | A1* | 12/2012 | Paterok | A47C 7/744 |
| | | | | 5/423 |
| 2013/0037063 | A1* | 2/2013 | King | A61L 2/07 |
| | | | | 134/31 |
| 2014/0137330 | A1* | 5/2014 | Lisi | A47C 31/007 |
| | | | | 5/694 |
| 2015/0096121 | A1* | 4/2015 | Scarleski | A47C 31/105 |
| | | | | 5/484 |
| 2015/0189966 | A1* | 7/2015 | Kim | A45D 19/14 |
| | | | | 4/517 |
| 2017/0190494 | A1* | 7/2017 | Stickler | A47C 23/00 |

* cited by examiner

METHOD AND APPARATUS FOR ON-SITE MICROBIAL REMEDIATION AND SANITIZATION OF HOUSEHOLD ITEMS

BRIEF DESCRIPTION OF THE DISCLOSURE

The present invention pertains generally to the field of remediating and sanitizing household items. In particular the invention relates to a method and apparatus for remediating and sanitizing household items on-site using a remediation solution that can be disbursed using apparatus that includes a vacuum, a fogger, a vacuum bag, and a blower to perform both vacuum and fogging steps to infuse the items with the remediation solution so as to remove and destroy microbials from such items.

BACKGROUND OF THE INVENTION

The present invention pertains to a system and method for remediating and sanitizing household items. There has long been a need to remove microbials from household items that have been exposed to mold or water. In particular a need has existed to perform such removal at the site where such items are found, rather than having to transport them to a remediation facility.

In that household items in need of remediation can take many forms, including chairs, couches, beds, mattresses, box springs, cushions, etc., a particular need has developed for a readily portable system of hardware, along with a relatively quick and easy method for performing on-site remediation.

SUMMARY OF THE INVENTION

The present invention pertains to a system and method for remediating and sanitizing household items. In accordance with the invention the item in need of remediation is first prepared for exposure to a high vacuum environment. Such preparation may include bracing the item so that it is not damaged during subsequent steps in which it will be subjected to being enclosed in a plastic vacuum bag that is subjected to a sufficiently high vacuum that the item might be crushed. The item is next vacuumed using a HEPA vacuum to remove any microbials that are on the surface of the item. Then, the item is placed into a treatment or vacuum bag, which is sealed with the item inside. The vacuum bag has a "pipe" that extends through the vacuum bag. External to the vacuum bag a vacuum machine is connected to the pipe. Also connected to the pipe are a blower and a fogging machine, such as a glycol fogger. Each of the vacuum, the blower, and the fogging machine can be selectively connected to the pipe using shutoff valves. Once the vacuum bag is sealed, the remediation steps include evacuating the vacuum bag using the vacuum, then inflating the bag using the blower, adding a remediating fog to the bag, and then using the vacuum to collapse the bag, thereby infusing the remediating fog into the item. The steps of blowing up the bag, adding a remediating fog, and infusing by use of the vacuum may be repeated, as desired, after which the vacuum is released, and the treated item is removed from the vacuum bag.

DETAILED DESCRIPTION OF THE PREFERRED EMBODIMENTS

Figure 1:
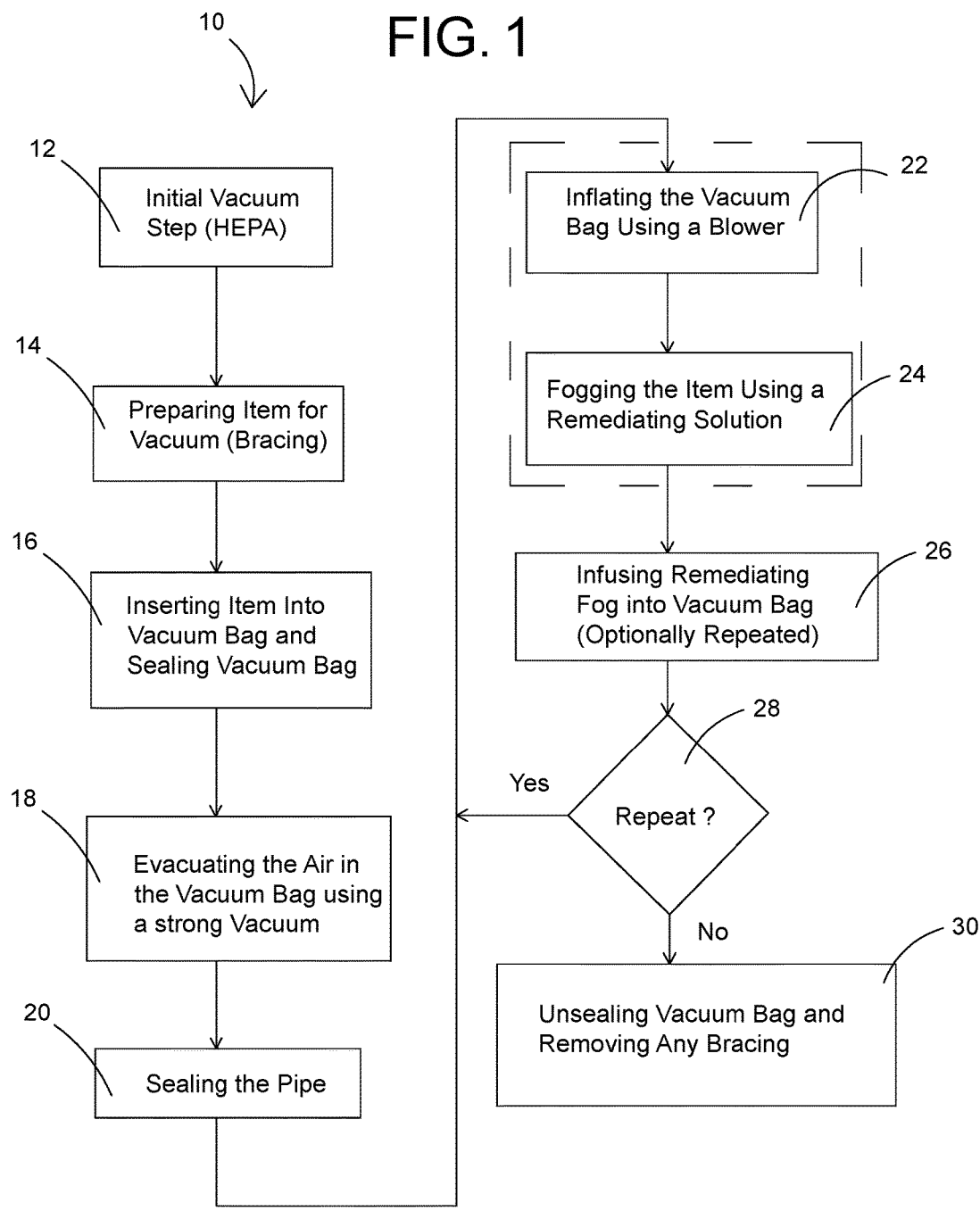
FIG. 1 illustrates the method of the preferred embodiment of the invention.
Figure 2:
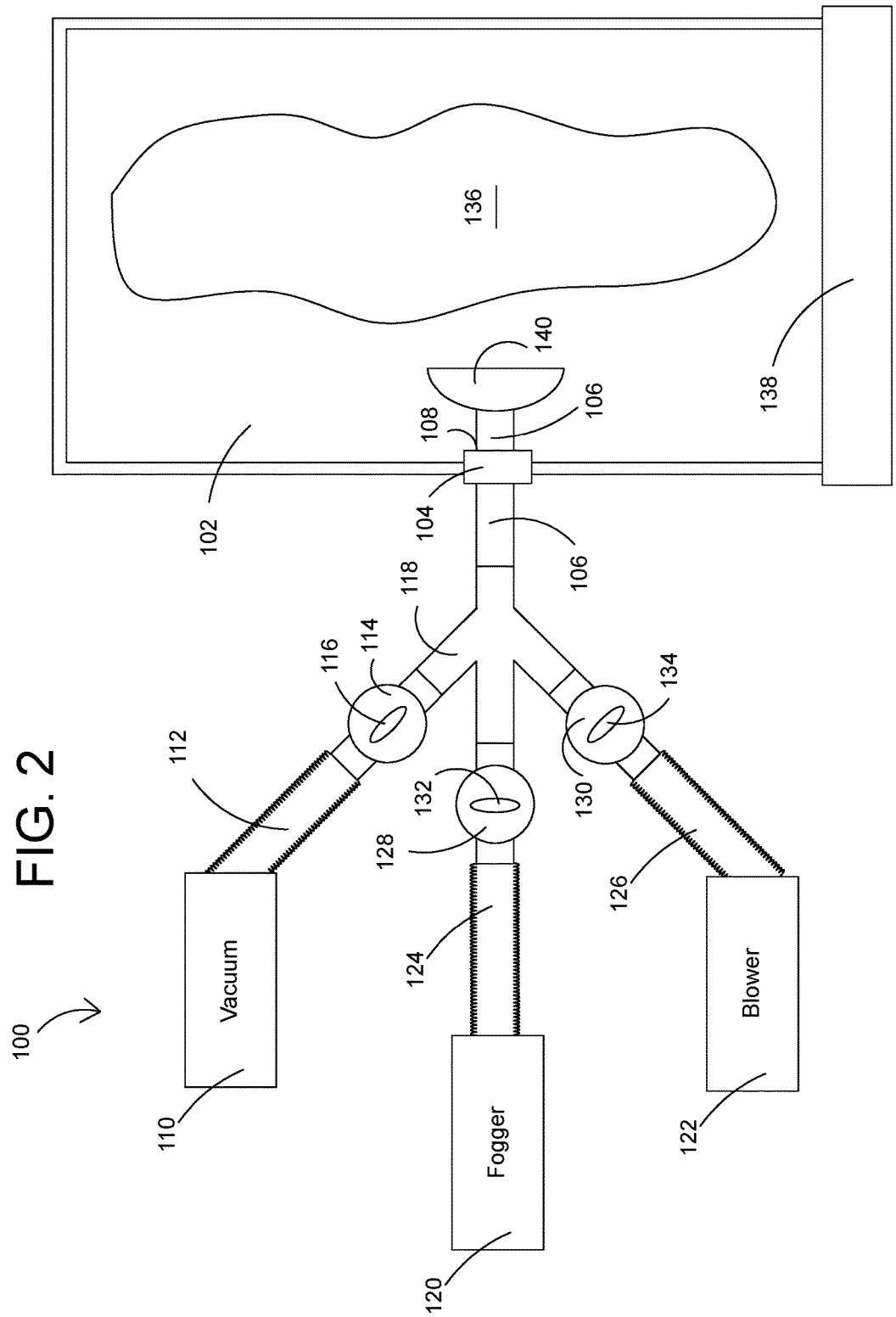
FIG. 2 illustrates the apparatus of the preferred embodiment of the invention.

The present invention relates to a method and apparatus for remediating household items that have been exposed to a detrimental microbial, such as mold. Referring to FIGS. 1 and 2 the method and the apparatus of the present invention are described. In particular, the method of the invention is illustrated in FIG. 1, while the apparatus used to perform the method of FIG. 1 is illustrated in FIG. 2.

In accordance with the present inventive method the item that is to be remediated undergoes a series of steps, as illustrated in the flow chart 10 of FIG. 1. The first step of the inventive method is an initial vacuum step 12, preferably employing a vacuum having a high-efficiency particulate (HEPA) arrestance filter (also called a high-efficiency particulate arresting filter or a high-efficiency particulate air filter) that is able to filter out very small particulates. In particular, aggressive vacuuming with a HEPA filter (A vacuum with a HEPA filter is also called a "HEPA vacuum".) will remove at least 99.97% of particles having a size of at least 0.3 µm. Nevertheless, the initial vacuum step 12 will generally remove only those particulates and microbials that are on the outer surface of an item being remediated.

In order to both remove additional (e.g., non-surface) microbials and to destroy the remaining microbials additional steps in accordance with the invention are required. As shown in FIG. 1 following the initial HEPA vacuuming step 12, the item to be remediated must be prepared to be placed into a vacuum bag, so the next step 14 is preparing the item for vacuum bagging. As vacuum bagging causes extreme pressure to be applied to an item, preparing the item in step 14 includes the application of any bracing that may be required to prevent particular items from being crushed when subjected to vacuum bagging. By way of example, if the item being treated is an upholstered chair, then (for reasons that will become clear) it is necessary to protect the legs of the chair in order to prevent the legs from being damaged during subsequent treatment steps that involve vacuum bagging. Protection of the legs of a chair can be accomplished by either suitable bracing or by having the legs protrude from the bag and sealing the bag around the protruding legs so that they are not subjected to the vacuum. Alternatively, if the item is a cushion, then part of step 14 would include opening any zippers or hook and loop (e.g., Velcro) fasteners on the cushion to be remediated so that access to the interior of such cushion is readily accomplished.

Once any needed bracing, or other preparation, has been accomplished in step 14, the next step 16 is inserting the item into a suitably sized vacuum bag made of a material (e.g., polyethelene) that fully encloses the item to be treated. Part of step 16 involves sealing the vacuum bag around the entire item, while leaving a pipe or hose extending out of the vacuum bag. As will be further explained hereinafter, in the preferred embodiment of the apparatus, a 1½" PVC pipe is used. The end of the pipe that is within the vacuum bag is preferably attached to a suitably sized and shaped nozzle such that the end of the pipe will not be obstructed during subsequent processing. By way of example, if PVC pipe is used, then a PVC floor (or "shower") drain fixture can be used on the end of the pipe that is within the vacuum bag.

After sealing the vacuum bag with the item enclosed therein in step 16, the next step 18 is evacuating the air from the vacuum bag preferably using a strong industrial vacuum. As the step 18 of evacuating air from the vacuum bag will collapse the vacuum bag around the item being treated, subjecting the item to up to 14.7 pounds per square inch of surface area of the vacuum bag, during step 18 the vacuum bag will collapse around, and squeeze the item with considerable force which is why the step 14 of preparing and bracing the item was required for those items that would otherwise be destructively crushed. By way of example, if an upholstered chair was not braced, it is highly likely that the pressure exerted on its legs and/or arms by the vacuum bag during the step 18 of evacuating air from the vacuum bag would destroy the legs and/or arms of the chair. On the other hand, items, such as cushions, pillows, or mattresses, that will be compressed during the evacuating step 18 without damage do not need to be braced, but preparing them may (i.e., for cushions) require that any zippers or hook and loop fasteners be opened so as to facilitate the later infusion of a remediating fog into those items. It is during this evacuating step 18 that air within the item, along with some of the microbials within the item will be extracted from the item, thereby further removing those microbials that were not removed from the surface of the item during the initial HEPA vacuuming step 12.

Once all of the air that the vacuum is capable of removing has been removed, and the vacuum bag has been collapsed over the item to the extent possible, the next step 20 is sealing the pipe (outside the vacuum bag) in order to maintain the collapsed state of the vacuum bag around the item. Following the pipe sealing step 20 a valve that opens a path between the vacuum and the pipe may be closed, and the vacuum may be turned off, whereby all of the air within the bag that the vacuum was capable of removing has been removed, and the vacuum bag has been fully collapsed over the item being treated.

At this point, the next step in accordance with the invention is to subject the item to a fogging solution. During the fogging step 24 a fog containing a remediating solution is introduced into the vacuum bag. Those skilled in the art will recognize that fogging machines generally do not include any type of blower or fan. Instead, the fog that is generated by a fogging machine results from heating the fogging solution within the fogging machine. Accordingly, in order to fully surround the item being remediated with an appropriate remediating fog it is desirable to inflate the vacuum bag by blowing air into, and inflating, the bag. This inflating step 22 is accomplished by using a blower that is attached to the pipe. As with the vacuum, a shutoff valve allows the blower to be isolated from the pipe.

The step of inflating the bag 22 helps to insure that the volume into which the fogging solution is to be injected has been maximized, so the next step is the actual fogging step 24, in which a fogging machine is used to fill the inflated vacuum bag with the remediating fogging solution. Those skilled in the art will recognize that the inflating and fogging steps 22, 24 can be combined, and that they will often take place simultaneously. As will be understood, and explained more fully below, the fogging solution is preferably an antimicrobial solution. With the bag inflated, the antimicrobial fogging solution will surround the item being treated.

At this point in the process, the item being remediated is surrounded by the antimicrobial fogging (remediating) solution, whereby the exposed surfaces of the item are covered by the fogging solution. In order to infuse the item with the fogging solution, the next step is an infusing step 26 that is accomplished by closing the fogging valve (along with the blower valve) and opening the vacuum valve, thereby causing the vacuum bag to again collapse around the item being remediated, while simultaneously causing the fogging solution to be infused into the item.

As will be obvious to those skilled in the art, the infusing step 26 is similar to the previously performed vacuum evacuation step 18, except that during the infusing step 26 the remediating fogging solution is forced into the item being remediated. While only a single infusing step is generally required, it has been found to be desirable to repeat the inflating and fogging steps 22, 24 at least once in order to fully force the fogging solution into the item being remediated. The decision to repeat those steps 22, 24 takes place at step 28. While the preferred method of the invention does not include repeating the infusing step 26 after any repetition of the inflating and fogging steps 22, 24, the infusing step 26 may, optionally, be repeated, as well.

Once the final infusing step 26 has been performed, and a decision has been made to not further repeat those steps (22, 24, 26) at step 28, then the vacuum bag can be unsealed, and atmospheric pressure can be introduced into the vacuum bag at step 30, and the item being remediated can be removed from the vacuum bag (part of step 30).

Referring now to FIG. 2, a schematic diagram illustrating the apparatus 100 of the present invention is shown. As illustrated, the apparatus 100 includes a sealable treatment or vacuum bag 102. The vacuum bag 102 is preferably made of a strong, preferably transparent, plastic material (such as polyethylene) having sufficient thickness (preferably at least 4 mil) so as to avoid punctures. In the preferred embodiment of the invention the vacuum bag 102 includes a sealed port 104 through which a pipe 106 passes into the bag 102 with an appropriate air tight seal 108 that prevents air from entering or leaving the bag around the pipe 106.

On the outside of the bag 102 the pipe 106 is attached to a vacuum 110, typically using a standard hose 112 that is connected to both the vacuum 110 and a vacuum valve 114. The vacuum valve 114 used in the preferred embodiment of the invention is a PVC ball valve having a shutoff handle 116 that can be turned 90 degrees. When the handle 116 is aligned in the direction of the valve 114 the valve 114 is "open", while the valve 114 is closed when the handle 116 is perpendicular to the direction of the valve 114. Use of the vacuum valve 114 allows the vacuum 110 to selectively have a path that goes from the vacuum 110 through the vacuum valve 114, then through one branch of a double wye connector 118, through the pipe 106 and into the bag 102. Alternatively, the vacuum 110 can be selectively isolated from the vacuum bag 102 by closing the valve 114. Those skilled in the art will recognize that the vacuum 110 should be a strong industrial vacuum whose output is vented outdoors so as to avoid the possibility that non-particulates be reintroduced into the site where remediation is taking place.

A fogging machine or fogger 120 (such as a glycol fogger) and a blower 122 (such as a hair dryer) are connected to the pipe 106 through hoses 124, 126 and ball (shutoff) valves 128, 130, respectively. As will be understood by those skilled in the art, with the vacuum 110, the fogger 120, and the blower 122 connected to the pipe 106 outside the bag 102, an operator may selectively connect one or more of the vacuum 110, the fogger machine 120, and/or the blower 122 to the pipe 106 by selectively opening and closing the respective valves 114, 128, 130.

The reason that the blower 22 is used is that typical fogging machines do not include any type of fan or blowing apparatus, but rely, merely, upon the generation of a "fog" resulting from the heating of a solution that typically contains glycol. Accordingly, it is preferable to connect the fogger 120 to the leg of the double wye 118 that provides the most direct (i.e., the straightest) path through the double wye 118 to the interior of the vacuum bag 102. Of course if a fan or blower was incorporated into the fogger 120, no additional blower 122 or blower valve 130 would be required, and a wye connector could replace the double wye 118.

While the term "pipe" has been used to refer to the apparatus passing through the bag 102, in practice the pipe 106 need not be entirely rigid. Those skilled in the art will recognize that PVC (or other plastic) can be used as the pipe 106. Further, those skilled in the art will recognize that flexible hoses 112, 124, 126 are typically connected between the vacuum 110 and the double wye 118, between the fogger 116 and the double wye 118, and/or the blower 122 and the double wye 118, whereby the schematic diagram shown in FIG. 2 is merely intended to illustrate the flow paths being used to perform the method of the present invention. As it is desirable to reduce internal resistance to the flow of the fog from the fogger 120, the flexible hose 124 can be replaced by a straight piece of PVC.

As set out above, it is desirable to be able to diffuse the remediating fogging solution through the pipe 106, and into the bag 102 so that it will surround the item 136 that has been sealed inside the bag 102 using a sealable opening 138 in the bag 102. In order to accomplish that, when the pipe 106 is actually comprised of a length of PVC pipe of the type used in plumbing applications and readily available at home centers, such as The Home Depot or Lowe's, a diffuser 140 is bonded to the interior end of the pipe 106. It has been found that a PVC fixture, such as a floor (or "shower") drain works well for diffusing the fogging solution inside the bag 102.

As will be understood, in order to conduct the steps of the present invention using the apparatus of FIG. 2, the following procedure is preferably conducted (with reference, also, to FIG. 1). First, a HEPA vacuum is used to thoroughly (and vigorously) vacuum the surface and all accessible portions of the item 136 being remediated (step 12). Thereafter, the item 136 is braced to the extent necessary (step 14) after which it is placed into the vacuum bag 102 through sealable opening 138 in the bag 102. The bag 102 is then sealed, i.e., by folding over the portions of the bag 102 including the sealable opening 138 and clamping the opening 138 shut (step 16).

With the vacuum valve 114 open and with the fogging valve 128 and blower valve 130 closed, the evacuating step 18 is accomplished, whereby as much air as can be extracted from the bag 102 using the vacuum 110 is removed from the bag 102, after which the vacuum valve 114 is closed, thereby sealing the pipe 106 leading into the bag 102 (at step 20).

Next, the blower 122 is turned on and blower valve 126 is opened in the inflating step 22, thereby preparing the bag 102 for infusion of the remediating solution. Once the bag 102 has been inflated, the blower valve 126 can be closed, and the fogging step 24 is accomplished by turning on the fogging machine 120 (which has been filled with the remediating fogging solution) and opening fogging valve 128 thereby surrounding the item 136 with the remediating fog (step 24). During the fogging step 24, the pipe 106 is moved around the item 136 being remediated to allow the diffuser 140 to subject the surfaces and exposed portions of the item 136 with the fogging solution, after which the fogging valve 128 can be closed.

At this point all of the shutoff valves 114, 128, 130 will be closed, so the system will be set up to repeat the inflating, fogging, and infusing steps 22, 24, 26, preferably at least once in order to fully force the fogging solution into the item 136 being remediated. Of course the fogging machine 116 will have to be refilled with fogging solution, as necessary. Once the infusing step 26 has been performed for the final time the seal 138 can be opened and atmospheric pressure can be introduced into the vacuum bag 102 at step 28, and the remediated item 136 can be removed from the vacuum bag 102.

At this point the overall method of the present invention has been described with reference to FIG. 1, while the apparatus of the preferred embodiment of the invention has and the method of using the apparatus of FIG. 2 to perform the inventive method of FIG. 1 has been described. However, those skilled in the art will recognize that a main feature of the invention is to infuse the fogging solution over and into the object being remediated. Accordingly, in accordance with the present invention, a preferred embodiment of a fogging solution, used to remediate mold, is described in the following table:

| Mold Remediating Solution (one gallon) | |
| --- | --- |
| Propylene Glycol | 10-102 oz. |
| CitriCidal Grapefruit Seed Extract "GSE" | 12-30 cc |
| Water | 100-1000 cc |
| CitriDrops ® | 5-20 cc |

NOTE:
CitriDrops ® is a proprietary formulation of extracts from grapefruit seed, lemon seed, lime seed, and tangerine seed, in glycerin, available from Microbalance Health Products (See www.microbalancehealthproducts.com).

In order to create one gallon of the remediating solution, the foregoing propylene glycol is added to a one-gallon container. Then the citrus seed extracts, and the CitriDrops® (collectively called the "agrumax" ingredients) are added. Finally, the remainder of the gallon container is filled with water, that may be filtered or distilled water, the container is then sealed, and the mixture is shaken.

Those skilled in the art will recognize that any suitable vacuum machines can be used to perform the method described herein. Accordingly, while the present invention has been described in connection with the use of a HEPA vacuum, it is possible to use a suitable "shop vac" or other vacuum, with or without a HEPA filter, although a HEPA vacuum is preferred for the initial vacuum step 12, although a strong industrial vacuum, preferably vented outdoors, is preferred for the subsequent steps 18, 26. As the purpose of the blower 122 is to inflate the vacuum bag 102, such inflation is required only because typical foggers, also called "glycol foggers", do not include their own blowers, so the blower 122 is needed to open space within the vacuum bag 102 to allow room for the fog generated by the fogger 120 to enter the bag 102 and surround the item 136.

With respect to the fogger 120 that is used, a commercial fogger, such as the Magnum 650 Fog Machine, having a 600 watt heat exchanger, a seven minute heat up time and a one liter fluid capacity is used in the preferred embodiment of the inventive method to produce the remedial fog. Alternatively, if a larger fluid capacity is needed, then a Rosco #1700 Fog Machine, having an 1190 watt heat exchanger, an eight minute heat up time and a 4 liter capacity can be used. Similarly, a Lite F/X Fogmaster Fog Machine, Model 1741 or other commercially available foggers can be used. As will be understood by those skilled in the art, a feature of fogging devices is that they use heat to create a "fog" having very small droplets that are readily air borne throughout the interior of the vacuum bag 102 for treating the item 136.

On the other hand, there are other foggers that have features that may make them desirable for use in particular applications. For example, there are foggers that enable the operator to adjust the particle (droplet) size, and that may be useful for fogging particular items. In particular, larger droplets help the fog settle faster, without as much drift, while smaller droplets are better for most indoor fogging applications in that they allow the smaller droplets to "float" (stay suspended in the air) longer in order to get into "hidden" areas. One such fogger, the Flex-A-Lite Model 2600 fogging machine made by B & G Equipment Company, P.O. Box 130, 6120 N. Rt. 611, Plumsteadville, Pa. 18949 (Phone 215-766-8811, Fax 215-766-8240), provides an adjustable flow rate of from about 0 to 9 ounces per minute, and it could be used to carry out the method of the present invention where adjustable flow rates and particle sizes could be desirable. Another fogger, the Flex-A-Lite Model 2600, includes a flexible hose that allows it to be connected to the pipe 106, and it also includes a flow adjustment knob that allows the operator to adjust the liquid flow rate to dispense materials at average droplet sizes under 20 microns (for a water based formulation at room temperature). Droplets of this size remain suspended in the air for extended periods of time, so they disperse into areas otherwise difficult to reach and treat. At higher flow rates, the average droplet size tends to increase to about 80 microns when the liquid flow is adjusted for maximum output. The larger sized droplets are dispersed by air flow and can settle on surfaces, which makes them particularly useful for coating the inside of heat ducts and similar items. As will be understood by those skilled in the art, the use of such other foggers would not depart from the spirit or scope of the present invention.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

We claim:

1. A method for remediating a crushable, air permeable, household item that may have been exposed to mold, comprising the steps of:

(a) preparing said item to prevent it from being crushed by bracing said item;

(b) sealing said item inside a sealable vacuum bag;

(c) evacuating air from the inside of said bag, said step of evacuating air from the inside of said bag causing the evacuation of air from within said air permeable item occurring after said step of preparing said item;

(d) introducing an antimocrobial remedial fog into said bag;

(e) infusing said antimicrobial remedial fog into said air permeable item; and (f) removing said item from said bag.

2. The method for remediating of claim 1 further comprising the step of vacuuming the surfaces of said item to remove surface microbials from said item prior to the step of sealing said item inside said bag.

3. The method for remediating of claim 2 wherein said step of vacuuming said item includes using a vacuum selected from the group consisting of a shop vacuum and a HEPA vacuum.

4. The method for remediating of claim 1 wherein said step of preparing said item includes opening any zippers or hook and loop fasteners that seal interior portions of said item.

5. The method for remediating of claim 1 wherein said step of evacuating air from said bag includes subjecting the interior of said vacuum bag to an externally applied vacuum.

6. The method for remediating of claim 5 wherein said step of evacuating air from said bag includes subjecting said interior of said vacuum bag to an externally applied vacuum from a vacuum selected from the group consisting of a HEPA vacuum and a shop vacuum.

7. The method for remediating of claim 1 further comprising the step of inflating said bag prior to said step of introducing a remedial fog into said bag.

8. The method for remediating of claim 1 wherein said step of introducing a remedial fog into said bag is accomplished by using a glycol fogger.

9. The method for remediating of claim 1 wherein said step of infusing said remedial fog into said item is accomplished by using an external vacuum selected from the group consisting of a HEPA vacuum and a shop vacuum to compress said bag over and around said item.

* * * * *